(12) United States Patent
Sitterlet

(10) Patent No.: US 9,304,073 B2
(45) Date of Patent: Apr. 5, 2016

(54) BOND STRENGTH TESTING APPARATUS AND METHOD FOR USING SAME

(71) Applicant: Pilkington Group Limited, Lathom (GB)

(72) Inventor: Charles Sitterlet, Northwood, OH (US)

(73) Assignee: Pilkington Group Limited, Lathom (GB)

( * ) Notice: Subject to any disclaimer, the term of this patent is extended or adjusted under 35 U.S.C. 154(b) by 318 days.

(21) Appl. No.: 14/171,863

(22) Filed: Feb. 4, 2014

(65) Prior Publication Data

US 2014/0216148 A1 Aug. 7, 2014

Related U.S. Application Data

(60) Provisional application No. 61/760,742, filed on Feb. 5, 2013.

(51) Int. Cl.
*G01N 19/04* (2006.01)

(52) U.S. Cl.
CPC ...................................... *G01N 19/04* (2013.01)

(58) Field of Classification Search
CPC .......... G01B 7/10; G01N 19/04; G01L 25/00; H01F 1/00; H01F 7/00; H01F 13/00
See application file for complete search history.

(56) References Cited

U.S. PATENT DOCUMENTS

| | | | | |
|---|---|---|---|---|
| 4,392,305 A | * | 7/1983 | Nix | G01B 7/105 324/230 |
| 4,404,839 A | | 9/1983 | Geisler | |
| 4,634,974 A | * | 1/1987 | Hunter | G01V 3/15 324/228 |
| 5,006,799 A | * | 4/1991 | Pfanstiehl | G01B 7/105 324/230 |
| 5,094,009 A | * | 3/1992 | Koch | G01B 7/105 324/230 |

* cited by examiner

*Primary Examiner* — John Fitzgerald
*Assistant Examiner* — Michael E Turbyfill
(74) *Attorney, Agent, or Firm* — Marshall & Melhorn, LLC

(57) ABSTRACT

An apparatus and method tests the strength of a bond between a substrate, especially a vehicle window, and an item bonded thereto. The apparatus includes a force transfer shaft having a first end extending from a housing and a second end positioned within the housing, a ferromagnetic member connected to the end of the force transfer shaft positioned within the housing, and a permanent magnet having a predetermined pull force secured to the housing proximate the ferromagnetic member.

18 Claims, 6 Drawing Sheets

BOND STRENGTH TESTING APPARATUS AND METHOD FOR USING SAME

RELATED APPLICATION

This application is claiming the benefit under 35 U.S.C. 119(e), of the provisional application filed Feb. 5, 2013 under 35 U.S.C. 111 (b) which was granted Ser. No. 61/760,742. This provisional application is incorporated herein by reference in its entirety.

BACKGROUND OF THE INVENTION

The invention relates to an apparatus for testing the strength of a bond between two materials. More particularly, the invention relates to a hand-held apparatus for testing the strength of, for example, an adhesive or solder bond between an item of hardware and a substrate material, especially a vehicle window. A method of using the apparatus is also an aspect of the invention.

Devices for testing the bond strength between two joined materials are known. Known testing devices, however, have been found to have a significant number of moving parts which wear out relatively quickly, and produce erratic results due both to such mechanical wear, as well as to improper use by the operator resulting from the operation of known devices in a non-repeatable manner.

Accordingly, a less complex, easier to use, and more reliable device for testing bond strength would be useful.

SUMMARY OF THE INVENTION

The invention relates to a hand-held apparatus for testing the strength of, for example, an adhesive or solder bond between an item of hardware and a substrate material such as a vehicle window. More particularly, the inventive apparatus includes a housing having an interior hollow chamber containing (1) a force transfer shaft which may extend substantially the length of the housing, (2) a return mechanism, such as one or more resilient springs, preferably enclosing the force transfer shaft, and (3) a ferromagnetic member connected to an end of the force transfer shaft movable at least partially within the hollow chamber. An end cap or second housing portion is connected to one end of the housing and such housing end cap contains a magnet such that the magnet is proximate the ferromagnetic member. Preferably, the end cap or multi-part housing is adjustable so as to be capable of varying the distance between the ferromagnetic member and the permanent magnet, which magnet has a predetermined magnetic pull force. A force application member is attached to an end of the force transfer shaft opposite that to which the ferromagnetic member is attached for engaging a bonded item for testing. A return stop member may optionally be attached to the end of the housing from which the force transfer shaft extends.

In a method of using the apparatus to test the strength of the bond between a substrate material and an item bonded to the substrate, more particularly, to determine whether the actual bond strength is equal to or greater than a desired minimum bond strength, a force application member of the apparatus is engaged with the bonded item. The force application member is used to exert a predetermined force on the bonded item, which exerted force is transferred to a force transfer shaft, which force transfer shaft is connected to a ferromagnetic member which is proximate a permanent magnet having a predetermined magnetic pull force. The force transfer shaft, the ferromagnetic member and the permanent magnet are located in one or more of a housing and, preferably an adjustable end cap or second housing member. The force transferred by the force transfer shaft causes the ferromagnetic member to disengage from the magnetic field created by the permanent magnet within the predetermined pull force range. The user of the apparatus then observes whether the bond between the bonded item and the substrate material exceeds the minimum desired bond strength.

BRIEF DESCRIPTION OF THE DRAWINGS

The above, as well as other advantages of the present invention will become readily apparent to those skilled in the art from the following detailed description when considered in the light of the accompanying drawings in which.

DETAILED DESCRIPTION OF THE INVENTION

Figure 1:
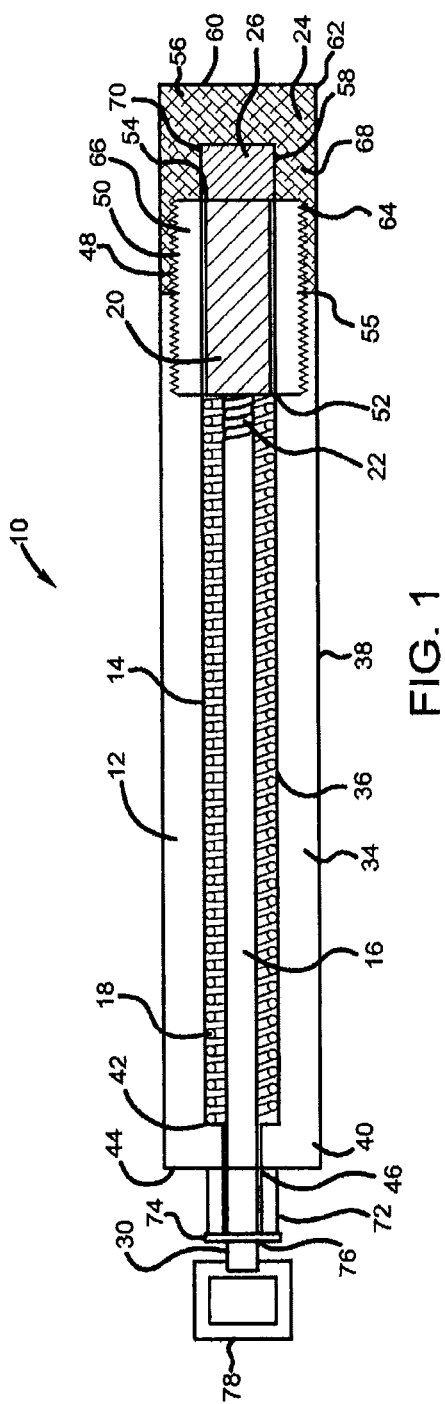
FIG. 1 is a cross-sectional view of a first embodiment of the apparatus according to the invention.

The invention relates to a hand-held apparatus for testing the strength of, for example, an adhesive or solder bond between an item of hardware and a substrate material such as a glass vehicle window.

More particularly, in an embodiment the apparatus 10 includes a housing 12 having an interior hollow chamber 14 containing (1) a force transfer shaft 16 extending substantially the length of the housing 12, (2) a return mechanism 18, for example, one or more resilient springs preferably enclosing the force transfer shaft 16 and (3) a ferromagnetic member 20 connected to a second end 22 of the force transfer shaft 16, and movable, at least partially, within the hollow chamber 14. An end cap 24 is connected to one end of the housing 12 and holds a permanent magnet 26 in a position such that the permanent magnet 26 is proximate the ferromagnetic member 20. Preferably, the end cap 24 is adjustable so as to be capable of varying the distance between the ferromagnetic member 20 and the permanent magnet 26, the permanent magnet 26 having a predetermined magnetic pull force. A force application member 28 is attached to a first end 30 of the force transfer shaft 16 for engaging a bonded item 32 for testing.

In one embodiment, shown in FIG. 1, the inventive apparatus 10 for testing the strength of a bond between two materials includes: a housing 12 having: substantially continuous side walls 34 having an inner surface 36 and an outer surface 38, a first end wall 40 having an inner surface 42 and an outer surface 44 with a bore 46 penetrating both inner and outer surfaces (42, 44), a second housing end wall 48 having an opening therein which preferably is a mechanically engaging portion 50, the substantially continuous side walls 34 and first and second end walls (40, 48) forming a hollow chamber 14.

Within the hollow chamber 14 is located: a force transfer shaft 16 extending substantially the length of the housing and having a first end 30 extending through the bore 46 penetrating the first end wall 40, and a second end 22 extending toward the second housing end wall 48, one or more return mechanisms 18 preferably enclosing the force transfer shaft 16, and a ferromagnetic member 20 having a first end 52 connected to the second end 22 of the force transfer shaft 16, and a second end 54 extending a predetermined length so as to be positioned proximate a permanent magnet 26.

An end cap 24 has a first end cap end wall 55, a substantially continuous second end cap end wall 56 having an inner surface 58 and an outer surface 60 and substantially continuous end cap side walls 62 having a substantially smooth continuous outer surface 64, and an inner surface comprising a mechanically engaging portion 66 complementary to the mechanically engaging portion 50 of the housing second end wall 48, as well as a non-mechanically engaging portion 68 which together with the inner surface 58 of the substantially continuous end cap end wall 56, form a magnet holding chamber 70 in which a permanent magnet 26 is disposed.

Optionally, a return stop member 72 is attached to the outer surface 44 of the first end wall 40 of the housing 16 and extends for a predetermined distance from the first end wall 40 in a configuration so as to enclose the first end 30 of the force transfer shaft 16 which extends outside the housing 12, and a return stop end cap 74 attached to the distal end of the return stop member 72, the return stop end cap 74 having an opening 76 therethrough, through which the first end 30 of the force transfer shaft 16 extends.

A force application member 78 is attached to the first end 30 of the force transfer shaft 16 for applying a testing force to a bonded item 32, for example an item of hardware bonded to a vehicle window 80.

Preferably, the mechanically engaging portions of the housing 12 and the end cap 24 are threaded so as to be complementarily mechanically engaging, more specifically, the housing 12 and the end cap 24 are adjustable one relative to the other. A threaded insert 66 may also be utilized to join the housing 12 and the end cap 24 and still provides for adjustability between the housing 12 and the end cap 24.

The return mechanism 18 can be any suitable mechanism, but preferably is one or more resilient spring. The strength of such resilient spring or springs is chosen so as to work in a complementary way with the chosen pull force of the permanent magnet 26. Generally it has been found to be desirable that the strength of the one or more return springs is less than the magnetic pull force of the permanent magnet 26.

In this embodiment, the ferromagnetic member 20 is capable of moving within the hollow chamber 14 during the bond strength testing process, but when the ferromagnetic member 20 is "at rest" and under the full extent of the influence of the magnetic pull force exerted by the permanent magnet 26, the ferromagnetic member 20 preferably is located partially in the housing 12 and partially within the end cap 24. In this embodiment the ferromagnetic member 20 may be in intimate contact with the permanent magnet 26.

Figure 2:
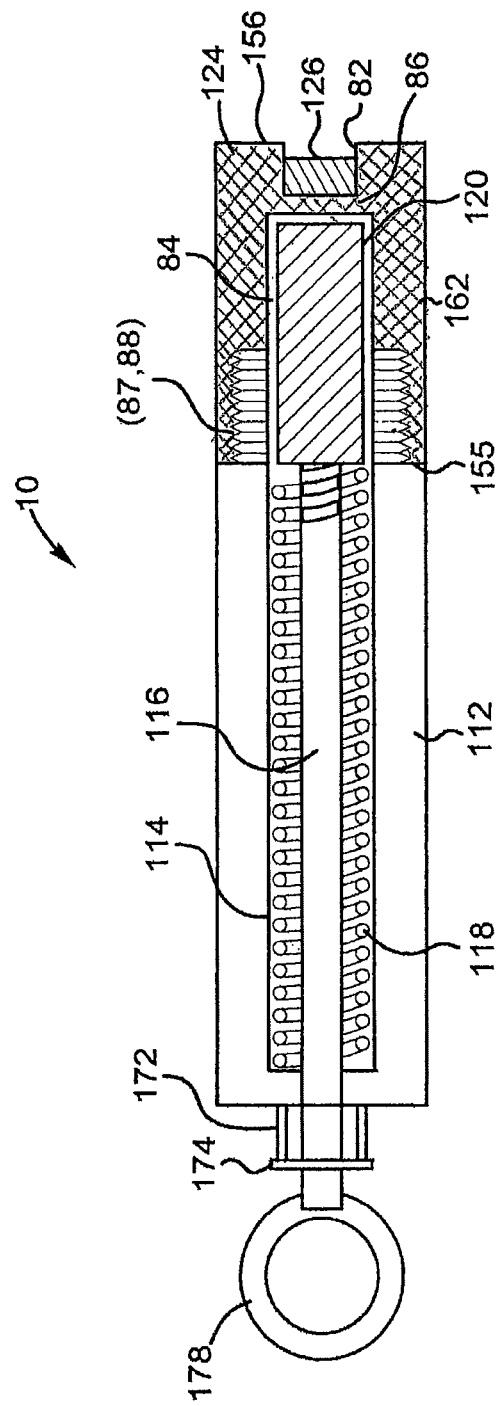
FIG. 2 is a cross-sectional view of an alternative embodiment of the apparatus according to the invention.

In a first embodiment shown in FIG. 2, the end cap 124 has substantially continuous end cap side walls 162 and a first end cap end wall 155 as in the previously described embodiment. In this first embodiment, however, the second end cap end wall 156 is not substantially continuous, but has a cut-out or recessed portion 82 which serves as the magnet holding chamber 170. In this configuration, in order for the ferromagnetic member 120 to be in the desired proximity to the permanent magnet 126 disposed in the magnet holding chamber 170, the ferromagnetic member 120 is preferably located in a hollow portion of the end cap 84 which is substantially continuous with the hollow chamber 114 in the housing 112 of the apparatus 10. In the first embodiment, it is preferred that the ferromagnetic member 120 and the permanent magnet 126 disposed in the recess 82 are separated by a portion of the end cap designated as an integral end cap separator portion 86. Preferably the integral end cap separator portion 86 has a fixed thickness defining the separation distance between the ferromagnetic member 120 and the permanent magnet 126. The end cap 124 of the first embodiment is desirably adjustable by complementary mechanically engaging portions (87, 88) of the housing 112 and the end cap 124, again for purposes of increasing or decreasing the distance between the ferromagnetic member 120 and the permanent magnet 126. In other particulars, the apparatus according to the first embodiment is substantially similar to the previously described embodiment.

Figure 3:
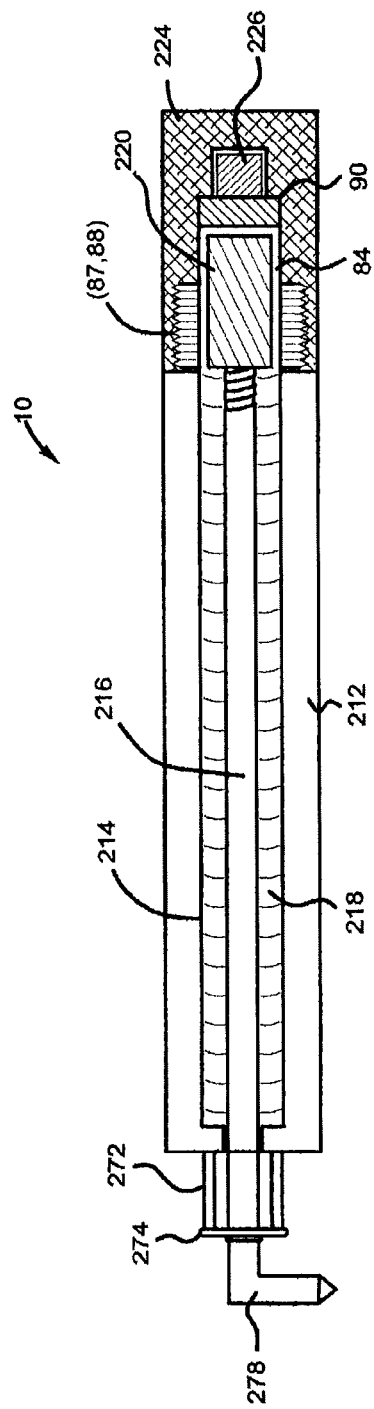
FIG. 3 is a cross-sectional view of another alternative embodiment of the apparatus according to the invention.

A second alternative embodiment of the apparatus is shown in FIG. 3. As shown in FIG. 3, the apparatus is similar in certain aspects to the first described embodiment and in certain aspects to the first embodiment. However, in the second alternative embodiment, rather than having an integral separator portion 86 between the permanent magnet 126 and the ferromagnetic member 120, a removable separator 90 made from a suitable dielectric material is utilized. Since the separator 90 is removable, the thickness of the separator 90 can be readily varied. The material from which the separator 90 is made can also be varied, for example, a resilient dielectric material could be selected. A resilient material may be advantageous to reduce the shock on, for example, the ferromagnetic member 220 and the magnet 226 resulting from the return portion of the operation of the apparatus during bond strength testing.

In any of the embodiments of the apparatus, the housing (12, 112, 212) can be any suitable geometric shape, but is preferably generally cylindrical. More preferably, the housing (12, 112, 212) is tubular. The housing (12, 112, 212) can be formed from any suitable material, but is preferably made from a metal such as aluminum or other non-ferrous metal.

The force transfer shaft (16, 116, 216) is generally cylindrical, preferably having a length substantially greater than its diameter and while many materials may be suitable, the force transfer shaft (16, 116, 216) is preferably made from a strong, dimensionally stable material such as stainless steel.

The return mechanism (18, 118, 218) can be, for example, a suitable hydraulic or pneumatic system, but is preferably one or more conventional resilient springs made from a metal such as steel and alloys thereof. The return mechanism (18, 118, 218) has a predetermined strength, but is preferably less than the pull force of the magnet.

The ferromagnetic member (20, 120, 220) is formed from a material that either is a source of a magnetic flux or is a conductor of a magnetic flux. The ferromagnetic material has some component of iron, nickel or cobalt. Preferably the ferromagnetic member (20, 120, 220) has a mass sufficient to counterbalance the maximum designated pull force of the permanent magnet (26, 126, 226). Alternatively, another properly selected permanent magnet can be used in place of the above-described ferromagnetic member (20, 120, 220).

The permanent magnet (26, 126, 226) can be any suitable permanent magnet, however a rare-earth magnet having a predetermined pull force expressed in pounds is preferred. More preferably, the pull force of the permanent magnet (26, 126, 226) is between 5 lbs and 80 lbs. Higher or lower pull forces may be desirable for certain applications. For purposes of this application, "pull force" is the force required to pull a magnet free from a flat steel plate using a force normal to the surface of the plate. Said another way, pull force is the limit of the holding power of a magnet.

The end cap (24, 124, 224) can be of any desired geometric shape and made from any suitable material. Preferably, the end cap (24, 124, 224) is made from a durable material such as a metal. Preferred metals include aluminum and other suitable non-ferrous metals.

The return stop member 72, 172, 272) and return stop member end cap (74, 174, 274) help to protect the first end wall of the housing 12, 112, 212) from damage during the return portion of the operation of the apparatus while conducting bond strength testing. The return stop member (72, 172, 272) and return stop member end cap (74, 174, 274) can be made from any suitable material, but are preferably made from a metal.

The force application member (78, 178, 278) can have any suitable configuration for engaging with a bonded item 32 and applying a testing force to the bonded item 32. Preferably, the force application member (78, 178, 278) is configured so that it is not likely to slip off the bonded item 32 to be tested. Several possible configurations of the force application member (78, 178, 278) are shown in FIGS. 1-4.

While the apparatus 10 can be utilized for a variety of purposes, a preferred use is to test whether an item of hardware 32, such as a clip, electrical connector, bracket, hinge or the like soldered to a glass vehicle window 80, meets the minimum desired strength for the bond between the item of hardware 32 and the surface of the glass 80.

A method of testing the strength of a bond between two materials utilizing the apparatus will now be described. It is desired to test whether the strength of, for example, the bond between one of the above-described items of hardware 32 and a substrate, such as a glass vehicle window 80, meet at least a desired minimum bond strength. To do so, an operator grasps the outer side wall surfaces 38, 138, 238) of the housing (12, 112, 212) of the apparatus 10 and engages the force application member (78, 178, 278) of the apparatus 10 with the bonded item 32. For the embodiments shown in FIGS. 1-3, a force is exerted on the bonded item 32 in a direction substantially normal to the substrate such as vehicle window 80. For the embodiment shown in FIG. 4, a force is exerted on the bonded item 32 in a direction substantially parallel to the substrate. The exerted force is transferred via the force application member (78, 178, 278) to a force transfer shaft (16, 116, 216) which is connected to a ferromagnetic member (20, 120, 220) proximate a permanent magnet (26, 126, 226) having a pull force within a predetermined range, for example, 5 lbs. to 80 lbs, although higher or lower pull forces may be desirable for some applications. The force exerted on the bonded item 32 causes the ferromagnetic member (20, 120, 220) to disengage from the magnetic field generated by the permanent magnet (26, 126, 226), which has the predetermined pull strength noted. The operator observes whether the actual strength of the bond between the bonded item 32 and the substrate exceeds the desired minimum bond strength. The exerted force is discontinued, allowing the force transfer shaft (16, 116, 216) to retract with shock-absorbing assistance from the return mechanism (18, 118, 218) and also allowing the ferromagnetic member (20, 120, 220) to re-engage with the magnetic field created by the permanent magnet (26, 126, 226), so as to be prepared for testing another bonded item 32. The apparatus shown in each of FIGS. 1-3, while differing in some aspects generally exert a pulling force in operation, and so may be characterized as a "pull-type" testing apparatus.

It is possible to apply the principles of the hand-held apparatus to create a magnetic testing fixture to test items with potentially higher bond strengths. In such an application, electromagnets might be used.

Figure 4:
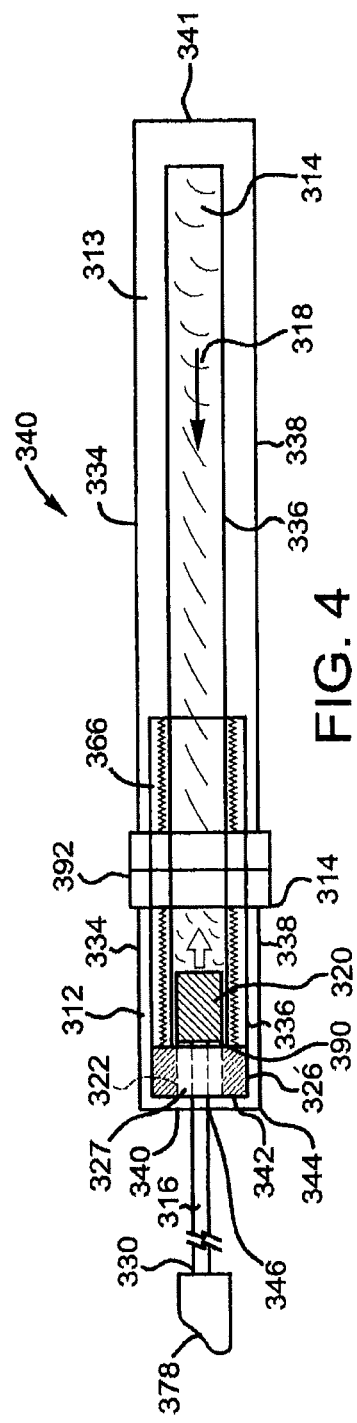
FIG. 4 is a cross-sectional view of a push-type embodiment of the apparatus according to the invention.

It is also within the scope of the invention to have a "push-type" testing apparatus 310 such as is shown in FIG. 4.

As contemplated, a push-type testing apparatus 310 includes a multi-part housing, preferably a two-part housing designated as first and second housing parts (312, 313). The first housing part 312 preferably has substantially continuous side walls 334 having inner and outer side wall surfaces (336, 338) and a first end wall 340 having inner and outer end wall surfaces (342, 344) both of which are penetrated by a bore 346 of a diameter sufficient to allow a force transfer shaft 316 to extend therethrough. Similarly, the second housing part 313 preferably has substantially continuous side walls 334 having inner and outer side wall surfaces (336, 338) and a second end wall 341. A hollow chamber 314 is defined by the side walls 334 and end walls (340, 341) of the first and second housing parts (312, 313). In a preferred configuration, the first and second housing parts (312, 313) are mechanically joined by a coupling member 392. A first end 330 of the force transfer shaft 316 preferably extends through the bore 346 in the first end wall 340 of the first housing part 312, and preferably has a force application member 378 connected to the first end 330 of the force transfer shaft 316. The second end 322 of the force transfer shaft 316 extends into the hollow chamber 314 for a distance equal to at least the length of the first housing part 312 but as necessary into the hollow chamber 314 in the second housing part 313. A permanent magnet 326 is preferably located in the hollow chamber 314 proximate the first end wall 340 of the first housing part 312. The permanent magnet 326 is preferably in a ring-type configuration, accordingly having a bore 327 therethrough, and through which bore 327 the second end 322 of the force transfer shaft 316 extends. The permanent magnet 326, as in the previously described embodiments of the inventive apparatus, is preferably a rare-earth magnet, more preferably a NIB magnet with a designated magnetic pull force in the range of 5 lbs. to 80 lbs., although other pull forces may be desirable for some applications. A ferromagnetic member 320 is connected to the second end 322 of the force transfer shaft 316 and is capable of movement within the hollow chamber 314 of the first and second housing parts (312, 313). In its "at rest" position, the ferromagnetic member 320 is influenced by the magnetic field created by the permanent magnet 326, and is preferably then, proximate the permanent magnet 326. It is also within the scope of the push-type embodiment that a ring-type ferromagnetic member may be located proximate the first end wall 340 of the first housing part 312 having a bore 327 therethrough. A permanent magnet 326 would then preferably be connected to the second end 322 of the force transfer shaft 316 so as to be capable of movement within the hollow chamber 314 of the first and second housing parts (312, 313). One or more return mechanisms 318 as previously described herein are likewise applicable to this "push-type" embodiment and are located in the hollow chamber 314 preferably extending at least the length of the second housing part 313.

It may be desirable for a predetermined portion of the inner wall surfaces 336 of the first or second housing parts to have threads formed therein so as to be able to mechanically engage with a threaded insert 366. The previously mentioned coupling member 392 may also interact with the threaded insert 366. An adjustment mechanism may be a feature of the two-part housing (312, 313) of the push-type testing apparatus 310. In order to absorb the shock of the ferromagnetic member 320 potentially striking the permanent magnet 326 as the ferromagnetic member 320 is moved by the one or more return mechanisms 318, it may be desirable to utilize a removable separator 390 placed between the permanent magnet 326 and the ferromagnetic member 320, which separator 390 is formed from a resilient dielectric material, as previously described herein in connection with the embodiment of the apparatus shown in FIG. 3.

Figure 6:
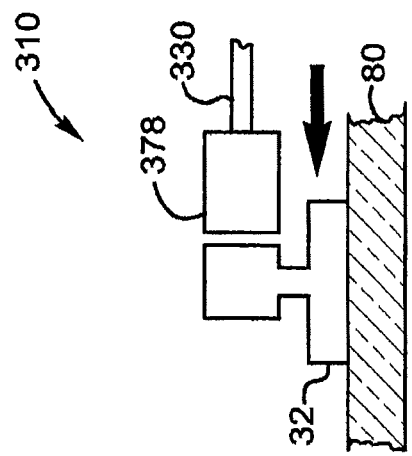
FIG. 6 is a schematic view of the method of operation of the embodiment of the invention as shown in FIG. 4.
Figure 5:
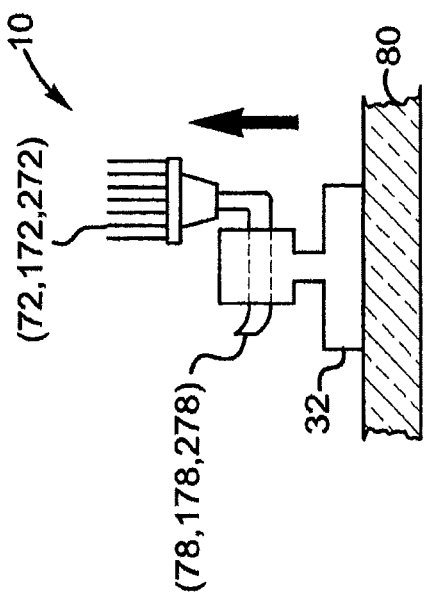
FIG. 5 is a schematic view of the method of operation of embodiments of the invention as shown in FIGS. 1-3.

In the embodiment shown in FIG. 4, the force exerted against a bonded item 32 is a pushing force exerted by the force application member 378 preferably in a direction substantially parallel to the substrate, such as a vehicle window 80 to which the item of hardware 32 is bonded, as illustrated in FIG. 6. This can be contrasted to the pull-type embodiments shown in FIGS. 1-3, which have a pulling force exerted by the force application member (78, 178, 278) against the bonded item 32 in a direction substantially normal to the substrate 80 to which the item of hardware is bonded 32, as illustrated in FIG. 5.

Figure 7:
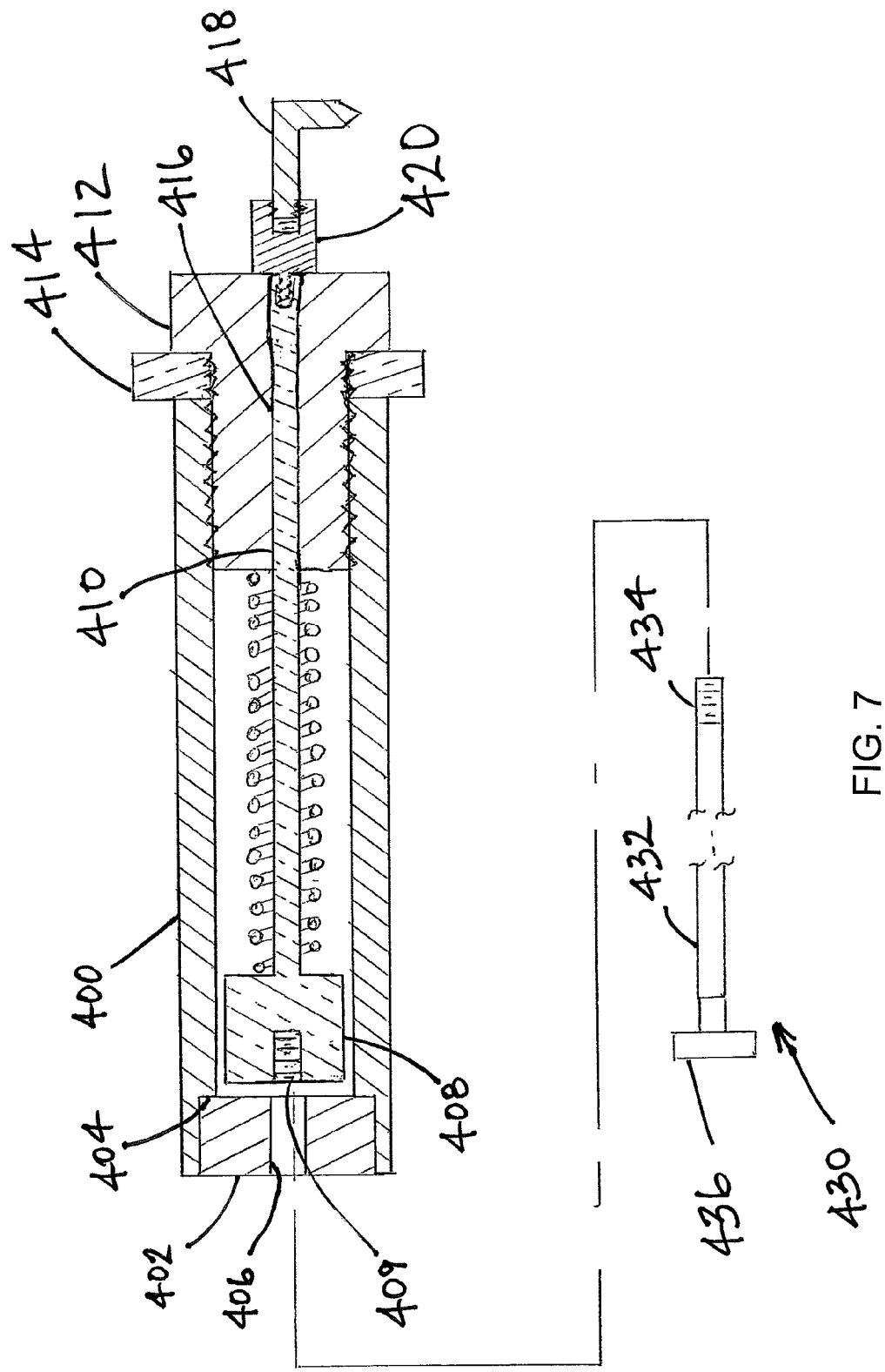
FIG. 7 is a cross-sectional, partially exploded view of a further embodiment of the apparatus according to the invention.

A further embodiment of the apparatus in accordance with the invention is shown in FIG. 7. A housing 400 is provided having a permanent magnet 402 secured at one end thereof. The housing 400 is preferably an elongate, hollow cylinder as shown in FIG. 7. At the end of the housing 400, there is section of increased internal diameter forming an annular shoulder 404 which engages at least a portion of an end of the permanent magnet 402, acting as a mechanical stop to prevent any axial movement of the permanent magnet 402 toward the opposite end of the housing. The permanent magnet 402 is preferably cylindrical in shape, and may be annular in shape so as to define an axially extending bore 406 therethrough. The permanent magnet 402 may be secured within the end of the housing 400 by any suitable means, for example by peening the end of the housing at one or more locations about the circumference thereof.

A ferromagnetic member 408 is positioned within the end of the housing 400 proximate the permanent magnet 402. The ferromagnetic member 408 is secured to or, as shown in FIG. 7, integrally formed at the end of a force transfer shaft 410. The ferromagnetic member 408 may optionally include a threaded bore 409 aligned with the optional bore in the permanent magnet 402. An adjustment head 412 and locking nut 414 are secured at the end of the housing 400 opposite the permanent magnet 402. The force transfer shaft 410 extends through a bore 416 formed through the adjustment head 412 to a selected force application member 418, preferably via a thread adapter 420 having one end threadedly secured to the end of the force transfer shaft 410 and the other end threadedly secured to the force application member 418.

The adjustment head 412 is preferably secured to the housing 400 via an externally threaded portion that mates with the internally threaded end portion of the housing 400. The locking nut 414 has internal threads that mate with the externally threaded portion of the adjustment head 412 to selectively fix the position of the adjustment head 412 relative to the housing 400. The end of the thread adapter 420 abuts the end of the adjustment head 412 to set the position of the ferromagnetic member 408 relative to the permanent magnet 402.

The embodiment of FIG. 7 may optionally include an attachment 430 to allow its use as a push-type tester. The optional attachment 430 includes a non-magnetic shaft 432 having a threaded end 434 which may be introduced through the bore in the permanent magnet 402 to threadedly mate with the threaded bore 409 formed in the ferromagnetic member 408. The opposite end of the shaft 432 can then be provided with any suitable force application member 436.

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed is:

1. An apparatus for testing the strength of a bond between two materials comprising:
    a housing containing a force transfer shaft;
    a ferromagnetic member connected to an end of the force transfer shaft;
    a permanent magnet secured at one end of the housing such that the magnet is proximate the ferromagnetic member; and
    a force application member attached to the opposite end of the force transfer shaft from the end to which the ferromagnetic member is connected for engaging a bonded item for testing.

2. The apparatus defined in claim 1, further comprising a return mechanism in the housing proximate at least a portion of the force transfer shaft.

3. The apparatus defined in claim 1, wherein the permanent magnet is carried by an end cap secured the housing that is adjustable so as to be able to vary the distance between the ferromagnetic member and the permanent magnet.

4. The apparatus defined in claim 1, wherein the permanent magnet is a rare earth magnet.

5. The apparatus defined in claim 1, wherein the permanent magnet has a magnetic pull force of between 5 and 80 lbs.

6. The apparatus defined in claim 1, further comprising a return stop member attached to the second end of the housing.

7. The apparatus defined in claim 6, wherein the return mechanism comprises one or more resilient springs.

8. The apparatus defined in claim 7, wherein the resilient spring exerts a force less than the magnetic pull force created by the permanent magnet.

9. An apparatus for testing the strength of a bond between two materials comprising:
    a multi-part housing comprising a first housing part having substantially continuous side walls having inner and outer surfaces, a first end wall having inner and outer surfaces and a bore penetrating both inner and outer surfaces, and a second end wall having substantially continuous inner and outer surfaces, and a coupling member mechanically joining the first and second housing parts, the housing defining a hollow chamber enclosed by the substantially continuous side walls of the first and second housing parts and the first and second end walls;
    a first transfer shaft having a first end extending through the bore in the first end wall of the first housing part with a force application member connected thereto, and a second end extending into the hollow chamber;
    a permanent magnet secured proximate the first end wall of the first housing part, the permanent magnet having a bore through which the second end of the force transfer shaft also extends;
    a ferromagnetic member connected to the second end of the force transfer shaft; and
    one or more return mechanisms located in the hollow chamber and extending at least the length of the second housing part.

10. The apparatus defined in claim 9, wherein the permanent magnet comprises a ring-type magnet.

11. The apparatus defined in claim 9, wherein the permanent magnet is a rare-earth magnet having a magnetic pull force between 5 lbs. and 80 lbs.

12. The apparatus defined in claim 9, wherein at least a portion of the inner walls of the first and second housing parts are threaded.

13. A method of testing the strength of a bond between a substrate and an item, comprising:
   providing a substrate material having an item bonded to the substrate material;
   providing an apparatus comprising a force transfer shaft having a first end extending from a housing and a second end positioned within the housing, a ferromagnetic member connected to the end of the force transfer shaft positioned within the housing, and a permanent magnet having a predetermined pull force secured to the housing proximate the ferromagnetic member;
   engaging the item with the end of the force transfer shaft that is opposite from the end to which the ferromagnetic member is connected;
   exerting a sufficient force on the item in a predetermined direction relative to the substrate material so that the ferromagnetic member is caused to disengage from the magnetic field created by the permanent magnet;
   discontinuing the exerted force, allowing the force transfer shaft to retract, so as to allow the ferromagnetic member to re-engage with the magnetic field created by the permanent magnet.

14. The method defined in claim 13, wherein the force exerted on the bonded item by the force application member is in a direction substantially parallel to the substrate material.

15. The method defined in claim 13, wherein the force exerted on the bonded item by the force application member is in a direction substantially perpendicular to the substrate material.

16. The method defined in claim 13, wherein the force exerted on the bonded item by the force application member is a pulling force.

17. The method defined in claim 13, wherein the force exerted by the force application member is a pushing force.

18. The apparatus defined in claim 13, wherein the ferromagnetic member is separated from the permanent magnet by a removable separator comprising a resilient dielectric material.

* * * * *